US005792719A

United States Patent [19]
Eberle et al.

[11] Patent Number: 5,792,719
[45] Date of Patent: Aug. 11, 1998

[54] SUPPORTED CATALYST FOR GAS-PHASE OXIDATION REACTIONS

[75] Inventors: Hans-Juergen Eberle; Werner Wagner, both of Munich; Franz Grundei, Ebersberg; Erich Liebisch, Munich, all of Germany

[73] Assignee: Consortium Fur Elektrochenische Industrie GmbH, Munich, Germany

[21] Appl. No.: 643,023

[22] Filed: May 2, 1996

[30] Foreign Application Priority Data

May 24, 1995 [DE] Germany .................. 195 19 172.2

[51] Int. Cl.⁶ .................. B01J 27/224; B01J 27/228; B01J 27/135
[52] U.S. Cl. .................. 502/178; 502/179; 502/227
[58] Field of Search .................. 502/209, 179, 502/120, 114; 549/248, 239

[56] References Cited

U.S. PATENT DOCUMENTS

| | | |
|---|---|---|
| 2,157,965 | 5/1939 | Pongratz . |
| 3,509,179 | 4/1970 | Friedrichsen et al. . |
| 3,799,886 | 3/1974 | Felice et al. . |
| 4,036,783 | 7/1977 | Blechschmitt et al. . |
| 4,077,984 | 3/1978 | Blechschmitt et al. . |
| 4,282,116 | 8/1981 | Reuter et al. . |
| 4,284,571 | 8/1981 | Sato et al. . |
| 4,356,112 | 10/1982 | Nakanishi et al. . |
| 4,481,304 | 11/1984 | Sato et al. . |
| 4,665,200 | 5/1987 | Nakanishi et al. .......... 549/239 |

FOREIGN PATENT DOCUMENTS

| | | |
|---|---|---|
| 0163231 | 2/1990 | European Pat. Off. . |
| 2067088 | 7/1981 | United Kingdom . |

*Primary Examiner*—Gary P. Straub
*Assistant Examiner*—Tanaza Anne Boozer
*Attorney, Agent, or Firm*—Burgess, Ryan & Wayne

[57] ABSTRACT

The invention relates to a supported catalyst for gas-phase reactions having an inert support body and a surface coating comprising a) at least 5% by weight of silicon carbide,
b) from 5 to 90% by weight, calculated as oxide, of one or more titanium dioxide or zirconium oxide components or mixtures thereof,
c) from 1 to 50% by weight, calculated as $V_2O_5$, of one or more vanadium oxide components,
d) from 0 to 10% by weight, calculated as oxide, of one or more compounds of elements of the 1st and 5th main groups of the Periodic Table, and also a process for its preparation and its use.

11 Claims, No Drawings ns: 5,792,719

SUPPORTED CATALYST FOR GAS-PHASE OXIDATION REACTIONS

BACKGROUND OF THE INVENTION

1). Field of the Invention

The invention relates to supported catalysts for gas-phase oxidation reactions, a process for their preparation and also their use in gas-phase oxidation reactions.

2). Background Art

In the gas-phase oxidation of hydrocarbons, a mixture of the hydrocarbons with air or with oxygen-containing gases is customarily passed over a catalyst which is located, for example, in a multitube reactor which comprises a plurality of tubes filled with catalyst. For the purpose of heating them to the required reaction temperature, and also for cooling these strongly exothermic reactions, the tubes are surrounded by a salt melt. However, in these (exothermic) oxidation processes, increasing loading of the air with hydrocarbons to be oxidized results in increased formation of by-products as a result of total oxidation. This is because of temperature peaks occurring in the catalyst bed, known as hot spots, which are higher the greater the loading of the air with the hydrocarbons to be oxidized. These hot spots can become so great as to result in runaway behavior of the reactor, which leads to damage to or deactivation of the catalyst.

In the past, there have been many attempts to increase the selectivity of gas-phase oxidation by use of specific catalysts.

Supported catalysts for the gas-phase oxidation of hydrocarbons to give carboxylic anhydrides, the catalytically active surface coating of which catalysts consists essentially of titanium dioxide ($TiO_2$), preferably in the anatase modification, and divanadium pentoxide ($V_2O_5$), have been known for some time and, in comparison with support-free (homogeneous) catalysts of corresponding composition, have a series of advantages such as higher selectivity and better operating behavior in such exothermic reactions as the oxidation of o-xylene and/or naphthalene to give phthalic anhydride (PA).

Thus, U.S. Pat. No. 2,157,965 describes the oxidation of naphthalene to PA using catalysts which are prepared by spraying a mixed precipitation from an aqueous solution or suspension containing ammonium metavanadate and titanyl sulfate onto supports such as pumice and subsequent calcination. The disadvantages of these catalysts are the initially high proportion of total oxidation and their short lifetime.

Use of inert, nonporous supports such as magnesium silicate or porcelain and direct spraying on of $TiO_2$-containing suspensions containing vanadyl oxalate as vanadium component (De-C 14 42 590=U.S. Pat. No. 3,509,179) and use of two different $TiO_2$ components of which an anatase component has a BET surface area of 7–11 $m^2/g$ and a titanium dioxide hydrate component has a BET surface area of above 100 $m^2/g$ (DE-C3 21 06 796=U.S. Pat. No. 3,799,886) enabled the selectivity of the oxidation reaction and the lifetime of the catalysts to be improved.

The use of two-bed packages in the multitube reactor also enabled the maximum loading to be only slightly increased. For this purpose, the catalytic activity of the upper bed was damped by addition of alkali metals while the lower bed was activated by phosphorus doping. For this method of operation, DE-B 25 46 268 (U.S. Pat. No. 4,077,984) describes loading increases in the oxidation of o-xylene to phthalic anhydride from 42 to merely 60 g/standard $m^3$ of air. Similar results were observed in naphthalene oxidation.

DE-C 29 48 163 (U.S. Pat. No. 4,284,571) describes a catalyst whose catalytically active composition comprising $V_2O_5$, anatase $TiO_2$ and various promoters such as oxides of phosphorus, niobium, cesium and/or thallium is applied to a porous support comprising at least 80% of silicon carbide. The advantage of this supported catalyst is the lowering of the hot spot temperature by use of a $TiO_2$ component derived from ilmenite (BET surface area: 10–60$m^2/g$).

DE-C 30 45 624 (U.S. Pat. No. 4,356,112) discloses catalysts having improved heat stability, which catalysts lower the hot spot temperature in the oxidation of o-xylene or naphthalene. The catalysts are supported catalysts which have an active layer based on $TiO_2/V_2O_5$ containing $Nb_2O_5$, $Cs_2O$, $K_2O$, $P_2O_5$ and $Sb_2O_3$ on a porous support based on silicon carbide, with the heat stability being increased by the $Sb_2O_3$ content. A similar catalyst for preparing pyromellitic dianhydride (PMDA) is described in EP-B 163 231. The last-mentioned catalysts are calcined before use and accordingly have relatively low abrasion resistance which can lead to loss of catalytically active surface coating on charging into industrial reactors. To improve the adhesion of the active layer to the porous SiC support, it is recommended that the active layer be mixed with metallic or ceramic whiskers having defined geometric dimensions. All these catalysts based on porous SiC supports have the disadvantage of the high price and the difficult reutilization of the support.

SUMMARY OF THE INVENTION

It is therefore an object of the invention to find improved supported catalysts for the air oxidation of, especially, aromatic hydrocarbons, in particular for the oxidation of naphthalene or a mixture of naphthalene and o-xylene to give PA or for the oxidation of 1,2,4,5-tetramethylbenzene (durene) to give PMDA, which catalysts are suitable for industrial reactors and give the desired reaction product in high yields. A particular focal point of the object is to develop catalysts which can react high hydrocarbon loadings of the reaction air, if possible even in the initial phase, without damage to the catalyst, so that even at high loadings a hot spot temperature (highest temperature in the catalyst bed) of 500° C. is not exceeded.

Surprisingly, this object can be achieved by means of a supported catalyst comprising a nonporous, inert support body and a surface coating in which part of the $TiO_2$ active component is replaced by SiC powder.

The invention provides a supported catalyst for gas-phase reactions having an inert support body and a surface coating comprising a) at least 5% by weight of silicon carbide, b) from 5 to 90% by weight, calculated as oxide, of one or more titanium dioxide or zirconium oxide components or mixtures thereof, c) from 1 to 50% by weight, calculated as $V_2O_5$, of one or more vanadium oxide components, d) from 0 to 10% by weight, calculated as oxide, one or more compounds of elements of the 1st and 5th main groups of the Periodic Table, where the figures in percent by weight are each based on the total weight of the active compounds and add up to 100% by weight.

DESCRIPTION OF THE PREFERRED EMBODIMENTS

In principle, the support bodies can have any shape and surface structure. However, preference is given to regular-shaped, mechanically stable bodies such as spheres, rings, half rings, saddles, or honeycomb supports or supports provided with channels. The size of the support bodies is determined primarily by the dimension, especially the internal diameter, of the reaction tubes if the catalyst is used in multitube or tube-bundle reactors. The support diameter should then be between ½ and ⅒ of the internal diameter. Suitable materials are, for example, steatite, duranite, stoneware, porcelain, silicon dioxide, silicates, aluminum oxide, aluminates or mixtures of these materials. Preference is given to spheres or rings of support materials such as duranite or steatite.

The proportion of the active surface coating is 1–30% by weight, preferably 2–15% by weight, based on the total mass of the supported catalyst. The thickness of the surface coating is preferably from 10 to 120 μm. A suitable component a) of the surface coating is commercial silicon carbide powder having a particle size of preferably up to 100 μm, with very fine SiC powder being preferred. Very good results are obtained, for example, using SiC having a particle size of from 10 to 50 nm.

Preference is given to a proportion of from 10 to 75% by weight, in particular from 30 to 75% by weight, of silicon carbide, based on the total weight of the active components.

As component b), preference is-given to using pulverulent $TiO_2$ in the anatase modification and having a BET surface area of from 5 to 200 $m^2/g$. Preference is also given to using a titanium dioxide hydrate (hydroxyl-rich, microcrystalline anatase) having a BET surface area of more than 100 $m^2/g$ or a mixture of anatase having a BET surface area of 5–11 $m^2/g$ and titanium dioxide hydrate in a mixing ratio of preferably from 1:3 to 3:1. Preference is given to using a proportion of from 10 to 75% by weight, in particular from 20 to 65% by weight, of component b), calculated as oxide and based on the total weight of the active components.

Components c) which can be used are vanadium oxide or vanadium compounds which are converted into vanadium oxide on heating in air, individually or in the form of their mixtures. Preference is given to using $V_2O_5$ or $NH_4VO_3$. Preference is given to using a proportion of from 5 to 30% by weight of vanadium oxide component, calculated as $V_2O_5$ and based on the total weight of the active components.

Suitable components d) are, for example, alkali metal compounds such as $K_2O$, $Cs_2O$, $Cs_2CO_3$ in an amount of preferably from 0.01 to 1.0% by weight, in each case based on the total weight of the active components. Also suitable are compounds of phosphorus, antimony, bismuth, preferably their oxides, in an amount of preferably from 0.1 to 10% by weight, in each case based on the total weight of the active components. Particularly, preferred examples of the last-named group are $P_2O_5$, $(NH_4)_2HPO_4$, $Sb_2O_3$.

To prepare the supported catalysts, the support bodies are preferably coated with an aqueous slurry of a mixture of the active components or else the individual components, and dried, for example in a rotary tube furnace at 200°–300° C. Supported catalysts having excellent adhesion of the coatings, which is particularly important for transport and charging of the catalyst into the reactor, are obtained, for example, by applying an aqueous suspension containing the mixture or the individual components as well as, if desired, an organic binder uniformly to the support bodies. Preferred organic binders are copolymers, advantageously in the form of an aqueous dispersion, of vinyl acetate/vinyl laurate, vinyl acetate/acrylate, styrene/acrylate, vinyl acetate/maleate or vinyl acetate/ethylene. Binder amounts of 10–20% by weight, based on the solids content of the suspension, are quite sufficient. After the catalyst is charged into the reactor, these copolymers burn out quantitatively in the stream of air within a short time.

The supported catalysts are suitable, for example, for use as oxidation catalysts in the oxidation of aromatics or alkylaromatics or mixtures thereof for preparing the corresponding acid anhydrides, preferably for preparing phthalic anhydride (PA) by catalytic gas-phase oxidation of o-xylene or naphthalene or mixtures of o-xylene and naphthalene. A further preferred application is an oxidation catalyst in the preparation of pyromellitic dianhydride (PMDA) by catalytic gas-phase oxidation of 1,2,4,5-tetraalkylated benzenes (for example durene=1,2,4,5-tetramethylbenzene).

In the preparation of PA and PMDA, the respective starting materials are reacted with an oxygen-containing gas in the presence of the catalyst of the invention, preferably in fixed-bed reactors. Typical fixed-bed reactors are, for example, reaction tubes which are collected into tube-bundle reactors and are surrounded by a heat exchange medium. The reaction tubes are arranged vertically and the reaction mixture flows through them from the top. They comprise a material inert toward the heat exchange medium, catalyst, starting materials and products, generally steel, and have a length of from 2000 to 6000 mm, an internal diameter of from 10 to 30 mm and a wall thickness of from 1 to 4 mm. Heat exchange media which have been found to be useful in practice are salt mixtures, for example, a chloride-free melt of potassium nitrate and sodium nitrite.

The catalyst is introduced into the reaction tubes from the top and is fixed by means of holders fitted in the vicinity of the lower ends of the tubes. The bed depth can be between 900 and 3300 mm. The reaction tubes can, if desired, be charged in layers with support bodies of different shape and size and also different concentration and composition of the active components.

The reaction gas comprising starting hydrocarbons and an oxygen-containing gas, preferably air, is passed over the catalyst at a space velocity of from 800 to 8000 $h^{-1}$, preferably from 1000 to 6000 $h^{-1}$. The mixing ratio is here from 10 to 150 g of hydrocarbon per standard cubic meter of oxygen-containing gas.

After the reaction, the product formed is isolated from the reaction gas in a manner known per se by desublimation or by appropriate gas scrubbing using a suitable solvent.

The supported catalysts of the invention are distinguished from the oxidation catalysts known hitherto and based on $TiO_2/V_2O_5$ by part of the $TiO_2$ component being replaced by SiC.

It has been found that mixing SiC powder into the catalytically active surface coating of catalysts has a particularly advantageous effect on the operating behavior and the selectivity of catalysts. This applies particularly to the oxidation of naphthalene or of a mixture of naphthalene and o-xylene to give PA and to the oxidation of durene to give PMDA. SiC-containing catalysts give higher carboxylic anhydride yields at higher hydrocarbon loadings both in the naphthalene and/or o-xylene oxidation and in the durene oxidation.

Completely unexpectedly, replacement of part of the $TiO_2$ active component by SiC, which was hitherto known only as an inert filler, gives catalysts which are superior to the SiC-free catalysts used hitherto in respect of selectivity and maximum loading. The catalysts of the invention make higher loadings possible. The yields are significantly improved. The supported catalysts of the invention are insensitive to short-term stressing at temperatures above 600° C.

The following examples serve to illustrate the invention.

Catalyst Preparation

The amounts indicated in Table 1 of the active components were suspended in 400 ml of deionized water and stirred for 18 hours o as to achieve homogeneous dispersion. Before application of the mixture to the steatite support bodies indicated in Table 1, the organic binder, a copolymer of vinyl acetate and vinyl laurate, was added in the form of a 50% strength aqueous dispersion to the suspension. The s was subsequently applied to the support with evaporation of the water.

pared with the anatase-containing catalyst A (Comparative Example 1), catalyst B (Example 1) gave a 3% by weight improvement in the PA yield. At the same time, substantially higher naphthalene loadings with lower hot spot temperatures were possible using catalyst B (Example 1).

Very fine SiC (30 nm particle diameter, Example 2) made possible loadings of up to MV 90 with even lower HST. Example 2 evidences the great flexibility in the selection of the SiC particle size and the improvement in the effect with decreasing particle size.

In the durene oxidation (Comparative Example 2, Example 3) too, significantly higher loadings with lower hot spot temperatures were possible.

TABLE 1

Composition of the catalysts:

| Catalyst | A | B | C | D | E |
|---|---|---|---|---|---|
| Support | 7 × 4 × 4 mm rings 1225 g | 7 × 4 × 4 mm rings 1225 g | 7 × 4 × 4 mm rings 1225 g | 8 mm spheres 1000 g | 8 mm spheres 1000 g |
| $V_2O_5$ | 15.33 g | 15.12 g | 15.12 g | 19.6 g | 19.6 g |
| $TiO_2$ hydrate, BET surface area: >150 m$^2$/g | 22.29 g | 23.67 g | 23.67 g | 40.27 g | 40.27 g |
| SiC | — | 94.69 g | 94.69 g | — | 16.00 g |
| Particle diameter | — | 4 μm φ | 30 mm φ | — | 4 μm φ |
| Anatase, BET surface area: <10 m$^2$/g | 96.00 g | — | — | 16.00 g | — |
| Ground steatite Particle diameter | — | — | — | — | — |
| $Ca_2CO_3$ | 322.7 mg | 393.6 mg | 393.6 mg | — | — |
| $(NH_4)_2HPO_4$ | — | — | — | 6.35 g | 6.35 g |
| Dispersion | 42 g | 42 g | 42 g | 30 g | 30 g |

To test the suitability of the supported catalysts as oxidation catalysts, they were tested in the oxidation of naphthlene to give phthalic anhydride (Examples 1 and 2) and in the oxidation of durene to give PMDA (Example 3). Conventional catalysts based on $TiO_2/V_2O_5$ were used for comparison (Comparative Examples 1, 2).

The oxidation experiments were carried out in a reaction tube replacing an industrial scale. The length of the reaction tube was 3.3 m (filling height 2.8 m), its diameter was 25 mm. The temperature of the reactor was controlled using a circulated salt bath (eutectic, chloride-free melt of potassium nitrate and sodium nitrite). The amount of air fed in was 4 standard m$^3$/h. The purity of the starting materials was always above 99%.

TABLE 2

Results of the oxidation experiments: anatase-SiC comparison

| Example | Comparative Example 1 | Example 1 | Example 2 | Comparative Example 2 | Example 3 |
|---|---|---|---|---|---|
| Catalyst | A (anatase) | B (SiC) | C (SiC) | D (anatase) | E (SiC) |
| Starting material | N[4] | N | N | D[5] | D |
| MV (max)[1] [g/Nm$^3$] | 52 | 80 | 90 | 26 | 40 |
| SBT [°C][2] | 360 | 365 | 364 | 376 | 385 |
| HST [°C][3] | 470 | 450 | 446 | 482 | 461 |
| Pure yield [% by weight] | 98 | 101 | 100 | 80 | 80 |
| | PA | PA | PA | PMDA | PMDA |

[1] MV (max) is the maximum usable hydrocarbon loading of the air in g of hydrocarbon per standard m$^3$ of air.
[2] Salt bath temperature
[3] Hot spot temperature
[4] Naphthalene
[5] Durene Examples 1 and 2 show the advantages of SiC in the oxidation of naphthalene to give phthalic anhydride. Com-

TABLE 3

Composition of the catalysts: Anatase-SiC comparison for two-bed packings

| Catalyst | F | G | H |
|---|---|---|---|
| Support | 7 × 7 × 4 mm rings 1000 g | 7 × 7 × 4 mm rings 1000 g | 7 × 7 × 4 mm rings 1000 g |
| Packing Filling height | Upper packing 150 cm | Upper packing 150 cm | Lower packing 130 cm |
| $V_2O_5$ | 9.95 g | 10.23 g | 10.05 g |
| Ti hydrate | 17.60 g | 16.02 g | 19.63 g |
| SiC (particle φ) | — | 38.45 g (4 μm φ) | — |
| Anatase, BET <10 m$^2$/g | 14.19 g | 25.63 g | 56.08 g |
| $Ca_2CO_3$ | 220 mg | 222 mg | — |
| $(NH_4)_2HPO_4$ | — | — | 1.372 g |
| Dispersion | 35 g | 35 g | 35 g |

Even in the case of the two-bed packings comprising damped upper bed and activated lower bed which are now customary in industry, SiC shows its advantages. It can here be sufficient to provide only the upper packing, in which the hot spot zone is located, with SiC (catalyst G). This catalyst G (upper bed), in which 60% of the low surface area anatase component was replaced by SiC, could be loaded at 102 g/standard m$^3$ after an operation time of about 4 weeks, without hot spot temperatures above 470° C. occurring (Example 4). The same lower bed H was used for both Example 4 and Comparative Example 3.

TABLE 4

Results of the oxidation experiments:
Anatase-SiC/anatase comparison for two-bed packings

| Example | Comparative Example 3 | Example 4 |
|---|---|---|
| Catalyst | F/H (anatase) | G/H (SiC/anatase) |
| Starting material | N | N |
| MV (max) [g/Nm³] | 62 | 102 |
| SBT [°C.]²⁾ | 360 | 368 |
| HST [°C.] | 474 | 462 |
| PA pure yield [% by weight] | 98 | 99 |

We claim:

1. A supported catalyst for gas-phase reactions having an inert support body and a surface coating said surface coating comprising the active component, comprising
  a) at least 5% by weight of silicon carbide,
  b) from 5 to 90% by weight, calculated as oxide, of one or more titanium dioxide or zirconium oxide components or mixtures thereof
  c) from 1 to 50% by weight, calculated as $V_2O_5$, of one or more vanadium components, and
  d) from 0 to 10% by weight, calculated as oxide, of one or more compounds of elements of the 1st and 5th main groups of the Periodic Table.

2. A supported catalyst as claimed in claim 1, wherein from 10 to 75% by weight is SiC, based on the total weight of the active components, said SiC having a particle size of up to 100 µm are present.

3. A supported catalyst as claimed in claim 1, wherein from 10 to 75% by weight, based on the total weight of the active components, is an $TiO_2$.

4. A supported catalyst as claimed in claim 1, wherein from 5 to 30% by weight, based on the total weight of the active components, is an $V_2O_5$.

5. A supported catalyst as claimed in claim 1, wherein from 0.01 to 1.0% by weight, based on the total weight of the active components, is an one or more compounds selected from the group consisting of $K_2O$, $Cs_2O$, $Cs_2CO_3$, $P_2O_5$, $(NH_4)_2HPO_4$ and $Sb_2O_3$.

6. A supported catalyst as claimed in claim 1, wherein from 1 to 30% by weight, based on the total weight of the supported catalyst, of active composition containing the active components a) to d).

7. A process for preparing supported catalysts as claimed in claim 1, which comprises coating the support bodies with an aqueous slurry of a mixture of the active components or with aqueous slurries of the individual active components and drying them.

8. The process as claimed in claim 7, wherein an aqueous slurry containing the active components and an organic binder is applied uniformly to the support bodies.

9. In a process for the oxidation of aromatics or alkylaromatics or mixtures thereof in the presence of a supported catalyst to give the corresponding acid anhydrides, the improvement which comprises conducting the oxidation in the presence of the supported catalyst of claim 1.

10. In a process for the preparation of phthalic anhydride by catalytic gas-phase oxidation of o-xylene, naphthalene or mixtures thereof in the presence of a supported catalyst, the improvement which comprises conducting the oxidation in the presence of the supported catalyst of claim 1.

11. In a process for the preparation of pyromellitic dianhydride by catalytic gas-phase oxidation of 1,2,4,5-tetraalkylated benzenes in the presence of a supported catalyst, the improvement which comprises conducting the oxidation in the presence of the supported catalyst of claim 1.

* * * * *